United States Patent [19]
Sommer et al.
[11] 4,246,416
[45] Jan. 20, 1981

[54] CHEMICAL AGENTS

[75] Inventors: Harold Z. Sommer, Havre de Grace; George E. Wicks, Jr., Baltimore; Omer O. Owens, Abingdon, all of Md.

[73] Assignee: The United States of America as represented by the Secretary of the Army, Washington, D.C.

[21] Appl. No.: 687,398

[22] Filed: Dec. 1, 1967

[51] Int. Cl.[3] .......... C07D 213/62
[52] U.S. Cl. .......... 546/261; 424/263
[58] Field of Search .......... 260/296; 424/263, 300; 546/261

[56] References Cited

U.S. PATENT DOCUMENTS 3,188,955 6/1965 Brown .......... 102/24

*Primary Examiner*—Leland A. Sebastian
*Attorney, Agent, or Firm*—Nathan Edelberg; Robert P. Gibson

[57] ABSTRACT

New chemical compounds, bis quaternary carbamates, having the generic formula:

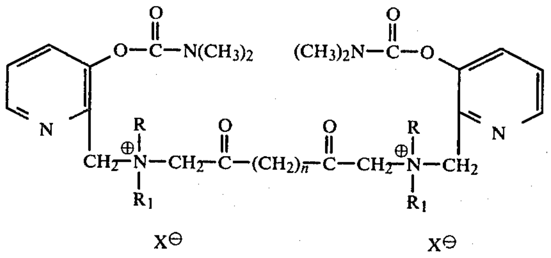

wherein X is one equivalent of a monovalent or polyvalent anion, wherein R and $R_1$ are aliphatic radicals selected from the group consisting of methyl, ethyl, propyl, isopropyl, butyl, isobutyl, tertiary butyl, pentyl and hexyl, and wherein n is 2-12, and having utility as incapacitating agents and in munitions.

2 Claims, No Drawings

CHEMICAL AGENTS

DEDICATORY CLAUSE

The invention described herein may be manufactured, used, and licensed by or for the Government for governmental purposes without the payment to us of any royalty thereon.

This invention relates to the synthesis of new toxic chemical compounds which are useful as chemical warfare agents. More particularly, our invention is concerned with novel compounds produced by means of a quaternizing reaction.

The chemical agents act mostly on the peripheral cholinergic nervous system which includes the motor nerves, the preganglionic fibers, the ganglia, the postganglionic parasympathetic fibers, and neuromuscular functions. The transmission of impulses along a nerve or from nerve fibers to muscle fibers or secretory cells or from one nerve fiber to another across synapses in ganglia is thought to involve chemical changes either directly or as the source of potential differences.

Quaternary ammonium compounds in general are known to be physiologically active materials. Mainly because of their positively charged "onium" centers they are attracted by anionic sites in animal tissues, particularly those situated at cell surfaces and interfaces. They can induce physiological responses that mimic or antagonize the action of acetylcholine as a result of their interaction with the various physiological receptor sites of acetylcholine, especially those at membranes of muscle cells. They also combine with enzymes such as acetylcholinesterase, other esterases, acetylcholineacetylase, etc., thus inhibiting their participation in the biological processes.

One of the significant anatomical differences between the neuromuscular junctions and other acetylcholine receptive sites is the absence of a membrane barrier or a sheath such as envelops the ganglia. The comparative ease of accessibility of the neuromuscular junctions to "onium" compounds contributes to their relatively fast onset of action and partly explains why in many instances relatively small doses suffice to evoke physiological actions that modify or interrupt normal neuromuscular impulse transmission.

Depending on their chemical structures different quaternary compounds interfere with the mechanism of impulse transmission in different manners and the final physiological effects can vary considerably. Some quaternary ammonium compounds are used as therapeutic agents, others are known to be lethal. The magnitude, accessibility, and distribution of the positive charges in quaternary compounds are believed to be the key factors in the determination of specificity of action. Recognition of these facts explains the strikingly different physiological behavior so often observed when structurally very closely related compounds are compared. The nature of the groups attached to the quaternary nitrogens influences the distribution of the cationic charges. The length and branching of aliphatic chains and the volume and configuration of aromatic and alicyclic rings have a bearing on the ease or difficulty of approach to the specific receptor sites. Electrophilic and nucleophilic centers in the molecule will insert their inductive effects on the positive charges and can also aid in the interaction with the "esteratic sites" of various enzymes. These sites are believed to be located in close vicinity to the anionic sites of the active centers. Substitution of different functional groups influences association and hydration and may considerably change the solubilities in physiological media. In bis-quaternary and poly-quaternary compounds the distance between the electric charges must be considered. These factors contribute to govern the rate and reversibility of the chemical reactions involved, and contribute to determine the final physiological responses.

Our chemical agents interfere with the normal process of neuromuscular impulse transmission and thus disrupt the propagation of impulses from nerves to muscles. We have also found these compounds to be extremely toxic at relatively low dose levels in various animals.

The principal object of this invention is to synthesize new lethal agents useful in chemical warfare in high yields; the agents being well suited for industrial scale manufacture. Other objects of and uses for the invention will in part be obvious and will in part appear hereinafter in the following detailed description thereof.

Our compounds may be employed in any munition suitable for handling a relatively non-volatile toxic agent such as bombs, shells, spray tanks, rockets, missiles, aerosol generators, and others.

In accordance with our invention a tertiary aminocarbamate was quaternized with an $\alpha,\alpha'$-diketohalide in a solvent, such as acetonitrile or acetone. The reaction mixture was allowed to stand at room temperature overnight. However, the mixture could stand for a few days if desired. A solid material precipitated out of the reaction mixture in the form of a viscous oily material after the addition of a solvent such as ethyl acetate. The precipitate solidified when the supernatant solvent mixture was decanted and stirred in a solvent such as acetone. The crude solid product thus obtained was purified either by recrystallization from a solvent such as acetonitrile or by dissolving it in a solvent such as acetonitrile or methanol, and subsequently treating the solution with decolorizing carbon, and precipitating the pure product by addition of a solvent such as ethyl acetate. The resultant white crystalline material constitutes the new compounds of the present invention which may be represented by the following generic formula:

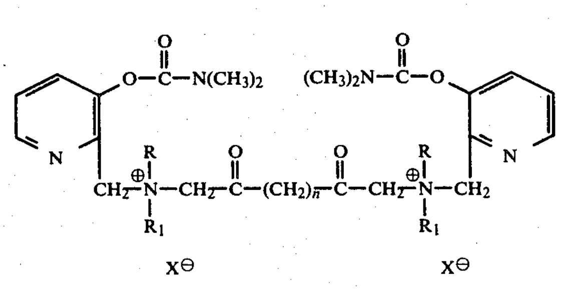

wherein X is one equivalent of a monovalent or polyvalent anion, wherein R, $R_1$ are aliphatic radicals selected from the group consisting of methyl, ethyl, propyl, isopropyl, butyl, isobutyl, tertiary butyl, pentyl and hexyl and wherein n is 2–12.

The procedure used for the preparation of the new toxic materials is schematically shown below:

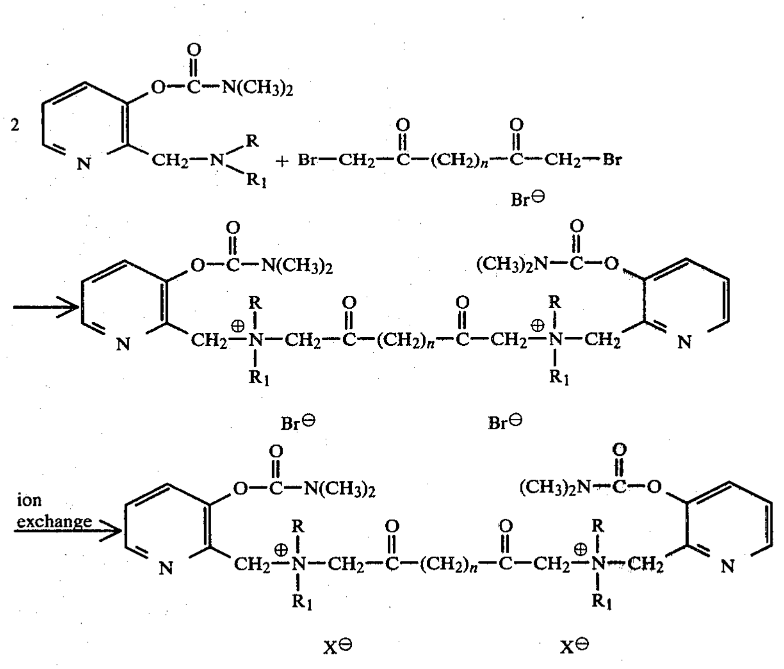

wherein X is a halide ion, preferably bromide, and wherein R, $R_1$ and n as defined above.

If compounds are desired in which X is other than a halide ion, the above quaternary compounds are treated with the desired acid by simple exchange reactions as set forth below.

EXAMPLE 1

A solution of 2-dimethylaminomethyl-3-dimethylcarbamoxypyridine (1.78 g) and 1,10-dibromodecane-2,9-dione (1.3 g) in 5 ml of acetonitrile was allowed to stand at room temperature for three days. The solid material that precipitated was collected on a filter and recrystallized from acetonitrile. Thus, 1.3 g of the pure product, 1,10-bis[N-(3-dimethylcarbamoxy-α-picolyl)-N,N-dimethylammonio]decane-2,9-dione dibromide, was obtained, as a crystalline solid, m.p. 169°-170° C.

Analysis for $C_{32}H_{50}Br_2N_6O_6$. Calcd: C, 49.6; H, 6.5; Br, 20.7; O, 12.4. Found: C, 49.5; H, 6.7; Br, 20.4; O, 12.5.

| Toxicity IV LD 50 | |
|---|---|
| Rabbits | Mice |
| 0.0027 mg/kg | 0.007 mg/kg |

EXAMPLE 2

A solution of 2-ethylmethylaminomethyl-3-dimethylcarbamoxypyridine (1.4 g) and 1,10-dibromodecane-2,9-dione (1.0 g) in 10 ml of acetonitrile was allowed to stand at room temperature overnight. The addition of about 50 ml of ethyl acetate caused an oily material to separate. The supernatant solvent mixture was decanted and the remaining oil stirred in about 50 ml of acetone. After a few minutes of stirring the oily material solidified. The solid material was then separated by filtration, dissolved in 30 ml of acetonitrile, and the resultant solution treated with decolorizing carbon. After about 80 ml of ethyl acetate were added a crystalline material precipitated which was collected on a filter and dried. Thus, 1.2 g of the pure product, 1,10-bis[N-(3-dimethylcarbamoxy-α-picolyl)-N-ethyl-N-methylammonio]decane-2,9-dione dibromide, was obtained, m.p. 158-163 (with decomposition).

Analysis for $C_{34}H_{54}Br_2N_6O_6\cdot\frac{1}{2}H_2O$. Calcd: C, 50.7; H, 6.7; Br, 19.6. Found: C, 50.3; H, 6.8; Br, 19.7.

| Toxicity IV $LD_{50}$ | |
|---|---|
| Rabbits | Mice |
| 0.004 mg/kg | 0.010 mg/kg |

EXAMPLE 3

A solution of 2-dimethylamino-3-dimethylcarbamoxypyridine (0.89 g) and 1,8-dibromooctane-2,7-dione (0.6 g) in 15 ml of acetone was allowed to stand at room temperature overnight. The precipitate that formed was collected on a filter and washed with acetonitrile. This crude material was purified by dissolving it in methanol, treating the solution with decolorizing carbon, and precipitating the product by addition of ethyl acetate. The dried crystalline product (0.6 g), 1,8-bis[N-(3-dimethylcarbamoxy-α-picolyl)-N,N-dimethylammonio]octane-2,7-dione dibromide, melted at 210°-211° C.

Anal. for $C_{30}H_{46}Br_2N_6O_6\cdot\frac{1}{2}H_2O$. Calcd: C, 47.7; H, 6.2; Br, 21.2; N, 11.1; O, 13.8. Found: C, 48.2; H, 6.2; Br, 20.9; N, 10.9; O, 13.6.

| Toxicity IV $LD_{50}$ | |
|---|---|
| Rabbits | Mice |
| 0.0027 mg/kg | 0.010 mg/kg |

The compounds that are representative of our invention are listed below by name and chemical structure.

1,6-bis[N-(3-dimethylcarbamoxy-α-picolyl)-N,N-dimethylammonio]hexane-2,5-dione dibromide.

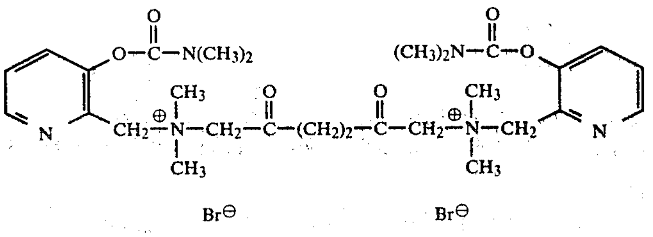

1,7-bis[N-(3-dimethylcarbamoxy-α-picolyl)-N,N-dimethylammonio]heptane-2,6-dione dibromide.

1,9-bis[N-(3-dimethylcarbamoxy-α-picolyl)-N,N-dimethylammonio]nonane-2,8-dione dibromide.

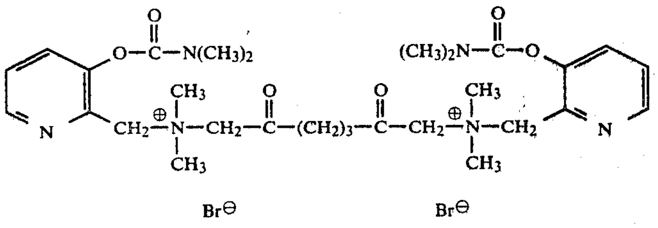

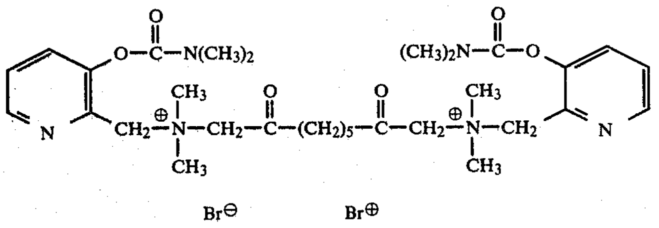

1,8-bis[N-(3-dimethylcarbamoxy-α-picolyl)-N,N-dimethylammonio]octane-2,7-dione dibromide.

1,10-bis[N-(3-dimethylcarbamoxy-α-picolyl)-N,N-dimethylammonio]decane-2,9-dione dibromide.

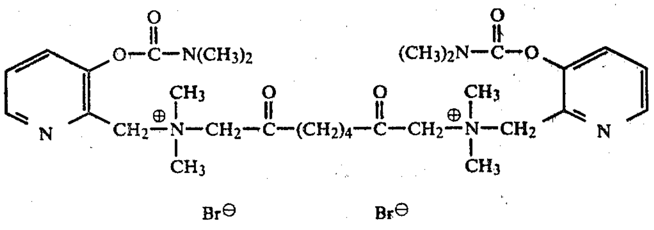

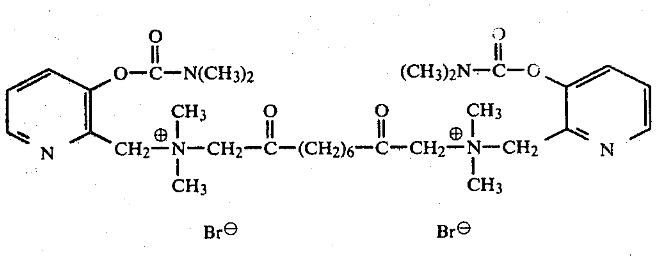

1,12-bis[N-(3-dimethylcarbamoxy-α-picolyl)-N,N-dimethylammonio]dodecane-2,11-dione dibromide.

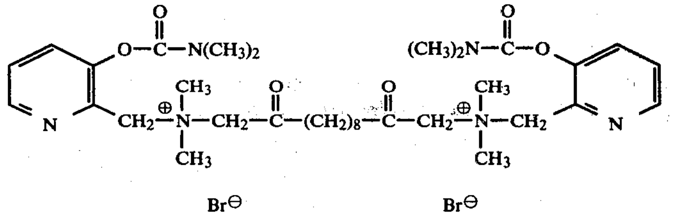

1,16-bis[N-(3-dimethylcarbamoxy-α-picolyl)-N,N-dimethylammonio]hexadecane-2,15-dione dibromide.

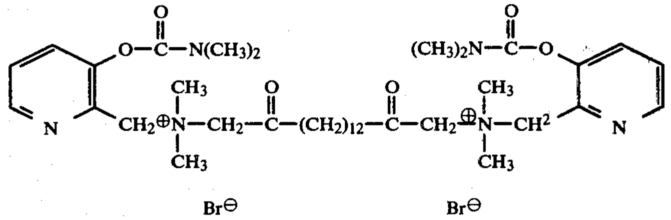

1,10-bis[N-(3-dimethylcarbamoxy-α-picolyl)-N-ethyl-N-methylammonio]decane-2,9-dione dibromide.

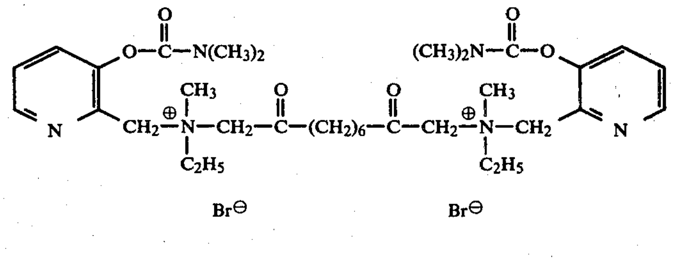

1,10-bis[N-(3-dimethylcarbamoxy-α-picolyl)-N,N-diethylammonio]decane-2,9-dione dibromide.

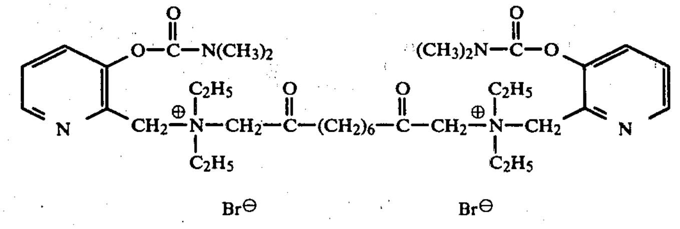

1,10-bis[N-(3-dimethylcarbamoxy-α-picolyl)-N-methyl-N-propylammonio]decane-2,9-dione dibromide.

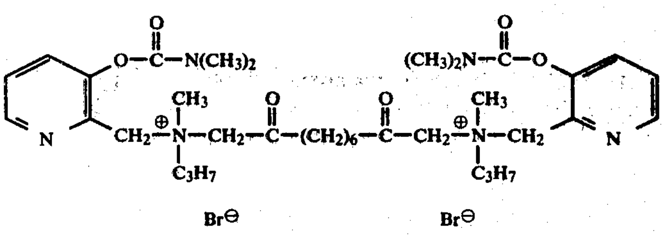

1,10-bis[N-(3-dimethylcarbamoxy-α-picolyl)-N-methyl-N-isopropylammonio]decane-2,9-dione dibromide.

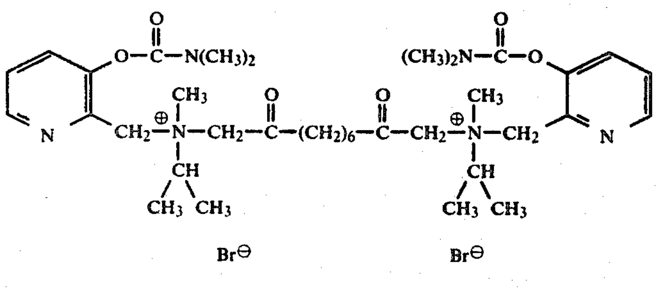

1,10-bis[N-(3-dimethylcarbamoxy-α-picolyl)-N-ethyl-N-propylammonio]decane-2,9-dione dibromide.

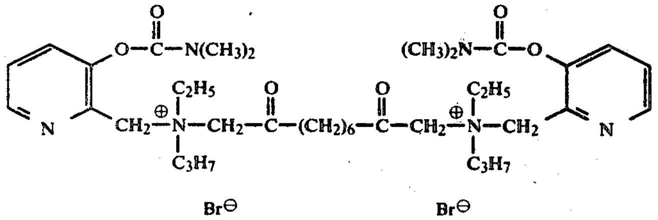

1,10-bis[N-(3-dimethylcarbamoxy-α-picolyl)-N,N-diisopropylammonio]decane-2,9-dione dibromide.

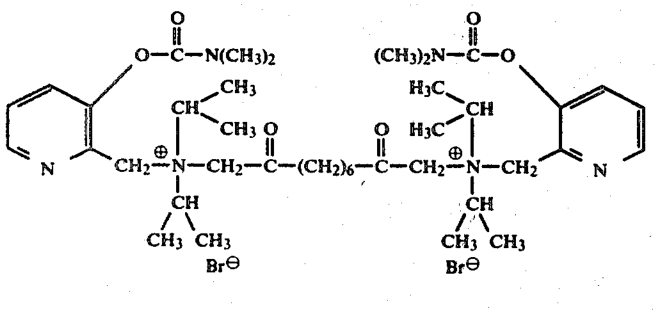

1,10-bis[N-(3-dimethylcarbamoxy-α-picolyl)-N-butyl-N-methylammonio]decane-2,9-dione dibromide.

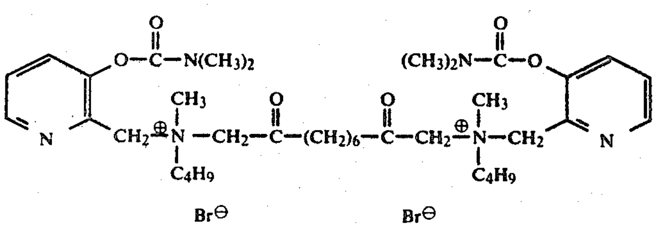

1,10-bis[N-(3-dimethylcarbamoxy-α-picolyl)-N-methyl-N-isobutylammonio]decane-2,9-dione dibromide.

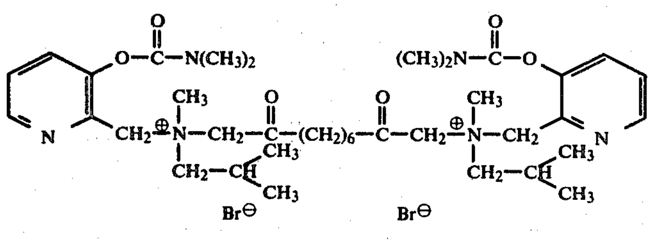

1,10-bis[N-(3-dimethylcarbamoxy-α-picolyl)-N-methyl-N-tertiarybutylammonio]decane-2,9-dione dibromide.

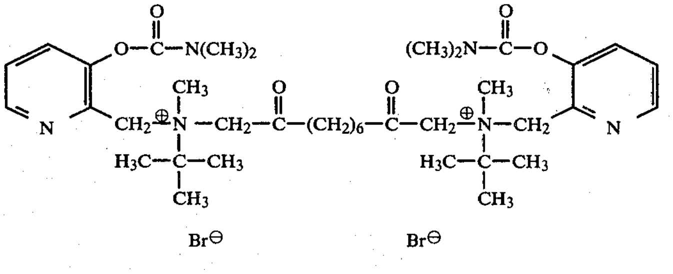

1,10-bis[N-(3-dimethylcarbamoxy-α-picolyl)-N-methyl-N-pentylammonio]decane-2,9-dione dibromide.

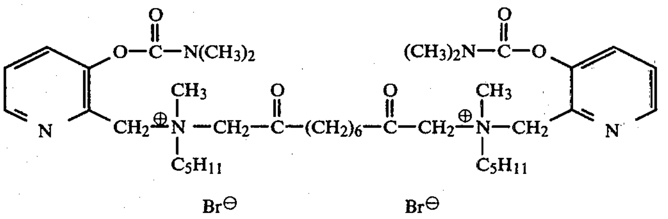

1,10-bis[N-(3-dimethylcarbamoxy-α-picolyl)-N-hexyl-N-methylammonio]decane-2,9-dione dibromide.

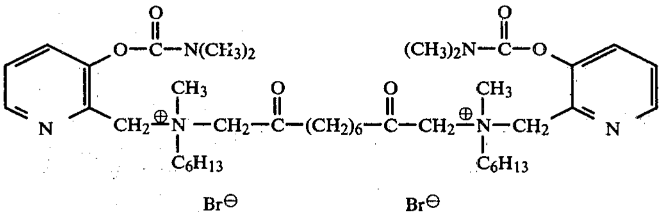

We have shown preferred compounds in which the anion is limited to the halogen moiety, in particular the bromide, since the bromoalkanes are good quaternizing agents. In general, however, it is only necessary that the anions merely have to meet the requirement of being capable of forming a stable salt with the quaternary nitrogen. Thus the halogen ions can be exchanged with other anions of relatively strong monovalent or polyvalent acid by conventional methods. For example, if $X^-$ is a bromide in the final product, a solution of the compound can be treated with a basic ion exchange resin or mixed with silver oxide and subsequently the desired acid is added to the quaternary hydroxide solution. Anions other than the halogens may also be obtained by metathesis with the halide form of the quaternary ammonium compound. Suitable as representations of $X^-$ are the anions hydrogen oxalate, perchlorate, nitrate, tetraphenylboronate, and hydrogen sulfate. Representative examples of these additional end products are:

1,10-bis[N-(3-dimethylcarbamoxy-α-picolyl)-N,N-dimethylammonio]decane-2,9-dione di(hydrogen oxalate).

1,10-bis[N-(3-dimethylcarbamoxy-α-picolyl)-N,N-dimethylammonio]decane-2,9-dione diperchlorate.

1,10-bis[N-(3-dimethylcarbamoxy-α-picolyl)-N,N-dimethylammonio]decane-2,9-dione dinitrate.

1,10-bis[N-(3-dimethylcarbamoxy-α-picolyl)-N,N-dimethylammonio]decane-2,9-dione di(tetraphenylboronate).

1,10-bis[N-(3-dimethylcarbamoxy-α-picolyl)-N,N-dimethylammonio]decane-2,9-dione di(hydrogen sulfate).

We claim:

1. New chemical compounds having the generic formula:

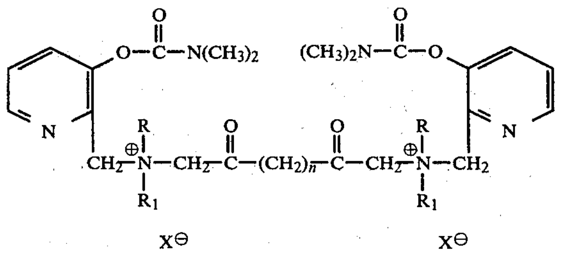

wherein X is one equivalent of an anion selected from the group consisting of monovalent and polyvalent anions, said anions being selected from the group consisting of halide, hydrogen oxalate, perchlorate, hydrogen sulfate, nitrate, and tetraphenylboronate, wherein R and $R_1$ are aliphatic radicals selected from the group consisting of methyl, ethyl, propyl, isopropyl, butyl, isobutyl, tertiary butyl, pentyl, and hexyl radicals, and wherein n is selected from 2–12.

2. New chemical compounds selected from the group of compounds having the names:

1,8-bis[N-(3-dimethylcarbamoxy-α-picolyl)-N,N-dimethylammonio]octane-2,7-dione dibromide;

1,10-bis[N-(3-dimethylcarbamoxy-α-picolyl)-N,N-dimethylammonio]decane-2,9-dione dibromide;

1,10-bis[N-(3-dimethylcarbamoxy-α-picolyl)-N-ethyl-N-methylammonio]decane-2,9-dione dibromide;

1,10-bis[N-(3-dimethylcarbamoxy-α-picolyl)-N-methyl-N-propylammonio]decane-2,9-dione dibromide;

1,10-bis[N-(3-dimethylcarbamoxy-α-picolyl)-N-methyl-N-isopropylammonio]decane-2,9-dione dibromide;

1,10-bis[N-(3-dimethylcarbamoxy-α-picolyl)-N-butyl-N-methylammonio]decane-2,9-dione dibromide;

1,10-bis[N-(3-dimethylcarbamoxy-α-picolyl)-N-methyl-N-tertiarybutylammonio]decane-2,9-dione dibromide;

1,10-bis[N-(3-dimethylcarbamoxy-α-picolyl)-N,N-diisopropylammonio]decane-2,9-dione dibromide.

* * * * *